Figure 1:
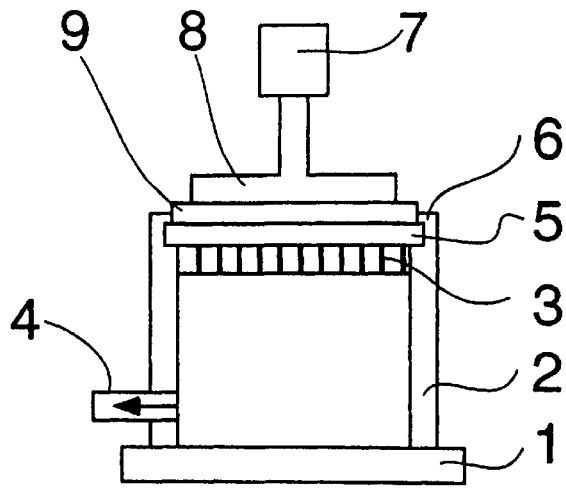

United States Patent [19]
Willenbacher et al.

[11] Patent Number: 6,098,450
[45] Date of Patent: Aug. 8, 2000

[54] DETERMINATION OF THE IMMOBILIZATION OF COLLOIDAL COATING DISPERSIONS

[75] Inventors: Norbert Willenbacher, Kirchheimbolanden; Harutyun Hanciogullari, Limburgerhof; Matthias Rädle, Weisenheim; Jürgen Ettmüller, Hassloch, all of Germany

[73] Assignee: BASF Aktiengelsellschaft, Germany

[21] Appl. No.: 09/115,798

[22] Filed: Jul. 15, 1998

[30] Foreign Application Priority Data

Jul. 30, 1997 [DE] Germany .............. 197 32 877

[51] Int. Cl.⁷ .......... G01N 11/14; G01N 33/26; G01N 33/32
[52] U.S. Cl. .......... 73/54.01; 73/54.22; 73/54.39
[58] Field of Search .............. 73/54.01, 54.39, 73/54.22, 54.37

[56] References Cited

U.S. PATENT DOCUMENTS 5,052,219 10/1991 Fery et al. .............. 73/54.39 X
5,319,958 6/1994 Date et al. .............. 73/54.39 X

FOREIGN PATENT DOCUMENTS 55-65136 5/1980 Japan .............. 73/54.39
60-179630 9/1985 Japan .............. 73/54.01

OTHER PUBLICATIONS

Baumeister et al., Wochenblatt fur Papierfabrikation 108 (5) (1980) 145–151.
Beck et al., Wochenblatt fur Papierfabrikation 111 (16) 1983, 561–565.
Sandas et al., Tappi 72 (12) 1989, 207–210.
Ramthun et al., Wochenblatt fur Papierfabrikation 122 (19) (1994), 745–750.

*Primary Examiner*—Daniel S. Larkin
*Attorney, Agent, or Firm*—Keil & Weinkauf

[57] ABSTRACT

In a proposed method for determining the immobilization of a colloidal coating dispersion which is applied to a porous substrate, the colloidal coating dispersion is applied to the porous substrate which forms a bounding surface of the measuring gap of a rheometer, and the change in the viscosity as a function of time is measured. The method is particularly suitable for measuring the immobilization of a paper coating slip on base paper.

12 Claims, 3 Drawing Sheets

DETERMINATION OF THE IMMOBILIZATION OF COLLOIDAL COATING DISPERSIONS

The present invention relates to a method for determining the immobilization of colloidal coating dispersions which are applied to a porous substrate, the use of the method and apparatuses for carrying out the method.

A knowledge of the change in the properties of colloidal coating dispersions as a function of time during application to porous substrates is essential for improving the technical processibility and optimizing novel formulations. Of particular interest in this context is the change in the viscosity of the colloidal coating dispersion during the application process and in particular a knowledge of the time when the viscosity abruptly increases. The salient point in the graph of the viscosity change as a function of time is defined as the immobilization point and the corresponding time as the immobilization time. Immobilization is defined as the state in which all flow and transport processes relating to the solids system are suppressed owing to the increased solids content.

A particular field of use is papermaking, where a knowledge of the immobilization of paper coating slips during application to base paper plays an important role with regard to the technical feasibility of novel formulations.

However, the immobilization of colloidal coating dispersions is also important in other areas, for example for adhesives or mortar, where the liquid phase of the coating dispersion may not be limited to water.

A commonly used method for characterizing the immobilization is the clay plate method (M. Baumeister and J. Weigl, Wochenblatt für Papierfabrikation 108 (5) (1980), 145–151). According to this method, a drop of a paper coating slip is placed on an unglazed clay plate and stirred with a spatula until the material has become solid. The time required is defined as the immobilization time.

The method has the disadvantages that the immobilization is not determined under conditions relevant to processing—the liquid-absorbing substrate is predetermined and a defined layer thickness cannot be specified—and the determination of the immobilization is subjective.

The above mentioned method was automated and made objective by the reflection measurement method [U. Beck et al., Wochenblatt für Papierfabrikation 111 (16) (1983), 561–565)]. The test set-up is supplemented by a photodiode which measures the development of the intensity of the reflection of a beam at the surface of the paper coating slip as a function of time. However, this test set-up, too, does not simulate conditions relevant in practice.

According to the Gradek method (S. E. Sandas, P. J. Salminen and D. E. Eklund, Tappi 72 (12) (1989), 207–210), the amount of water penetrating a defined base paper in a specific time and under a specific pressure is determined gravimetrically. Thus, what is measured is not the immobilization but the water loss through penetration into the base paper, with which the immobilization is associated. The method makes only a rough attempt to simulate conditions relevant in practice: slip and base paper are separated by a polycarbonate filter, no shear stress is applied and no process-relevant layer thickness is set.

A special filtration method and an adapted apparatus were furthermore developed (J. Ramthun, L. Reif, J. R öttger-Heinz, J. Waldi and G. Wallpott, Wochenblatt für Papierfabrikation 122 (19) (1994), 745–750): the paper coating slip is filtered through a filter of defined pore size at a predetermined pressure and with stirring, it also being possible to use base paper as the filter. The height of the speed-controllable stirrer above the filter can be varied by means of a micrometer. The passage of water through the filter is determined gravimetrically. In addition, the development of the power consumption of the stirrer as a function of time is measured and serves as a measure for the viscosity increase associated with the water loss. The method has the disadvantage that it is not possible to establish laminar shear flow under the stirrer or a process-relevant layer thickness since the layer above the lower stirrer edge is also dewatered.

It is an object of the present invention to provide a method which makes it possible to determine the immobilization of colloidal coating dispersions during application to a porous substrate under conditions which are relevant for processing: the layer thickness of the coating dispersion and the shear stresses occurring during the coating process can be approximated to the conditions relevant in practice; the apparatus for carrying out the method is robust and easy to handle, and the required technical means can be integrated as additional modules in commercial rotational rheometers.

We have found that this object is achieved, according to the invention, by a method for determining the immobilization of colloidal coating dispersions on application to a porous substrate by viscosity measurement, wherein the colloidal coating dispersion is applied to the porous substrate which forms a bounding surface of the measuring gap of a rheometer, and the change in the viscosity as a function of time is measured.

Preferably, the viscosity measurement can be carried out with specification of a constant shear stress or shear rate.

The novel method is particularly suitable for characterizing the immobilization of a paper coating slip by penetration of water into the base paper to be coated. However, the method is also suitable for characterizing other colloidal coating dispersions, for example, of adhesives or mortar. In these cases, the porous substrate appropriate in each case (eg. clay plate, glass frit) is used instead of the base paper as the rheometer base plate.

The layer thickness of the porous substrate and hence the height of the rheometer measuring gap can preferably be set at from 20 $\mu$m to 2 mm, particularly preferably from 50 $\mu$m to 500 $\mu$m.

In a preferred embodiment, it is additionally possible to approximate the applied pressure to the conditions relevant in practice by applying reduced pressure to that surface of the porous substrate which is opposite the surface to which the colloidal coating dispersion is applied.

Advantageously, the loss of liquid phase in the colloidal coating dispersion as a function of time can be monitored, preferably by means of a fiber optic scattered light measuring system, simultaneously with the characterization of the development of the viscosity as a function of time.

However, the loss of liquid phase can also be monitored by other known measuring methods, in particular by dielectric and optical spectroscopic methods.

According to the invention, the change in viscosity as a function of time is measured using a commercial rheometer controlled as a function of shear stress and modified in a manner such that the porous substrate which causes the immobilization by absorbing a part of the liquid phase forms a bounding surface of the rheometer gap.

Rheometers having a plate-plate geometry are particularly suitable, but rheometer apparatuses which have a plate-and-cone or a cylinder arrangement are also possible.

The invention is illustrated in more detail below by the drawing and the examples.

Figure 2A:
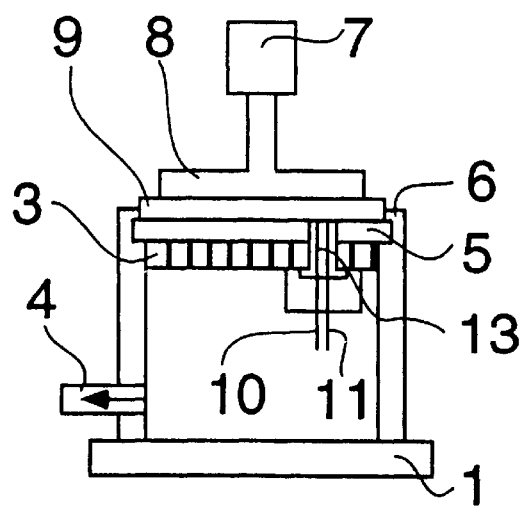
Figure 2B:
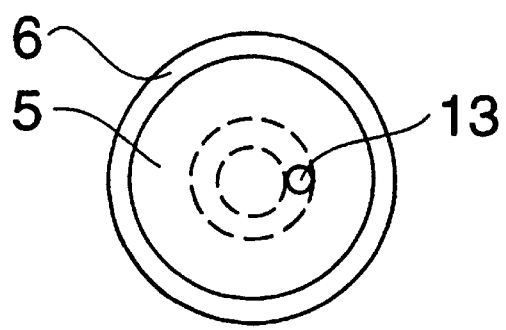
Figure 3:
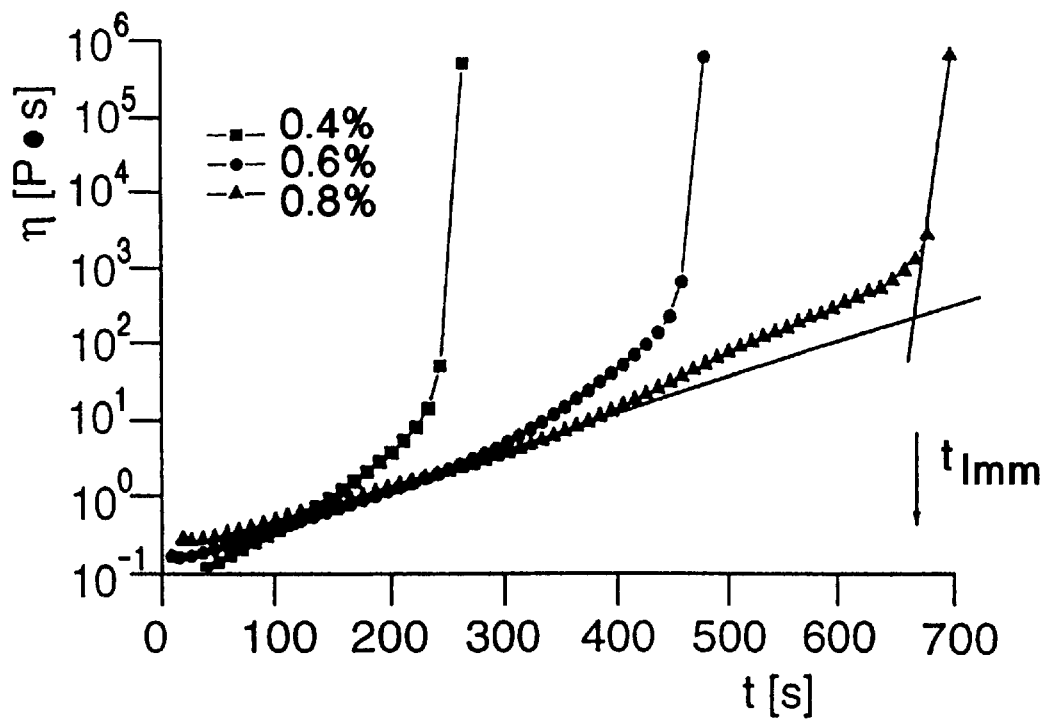
Figure 4:
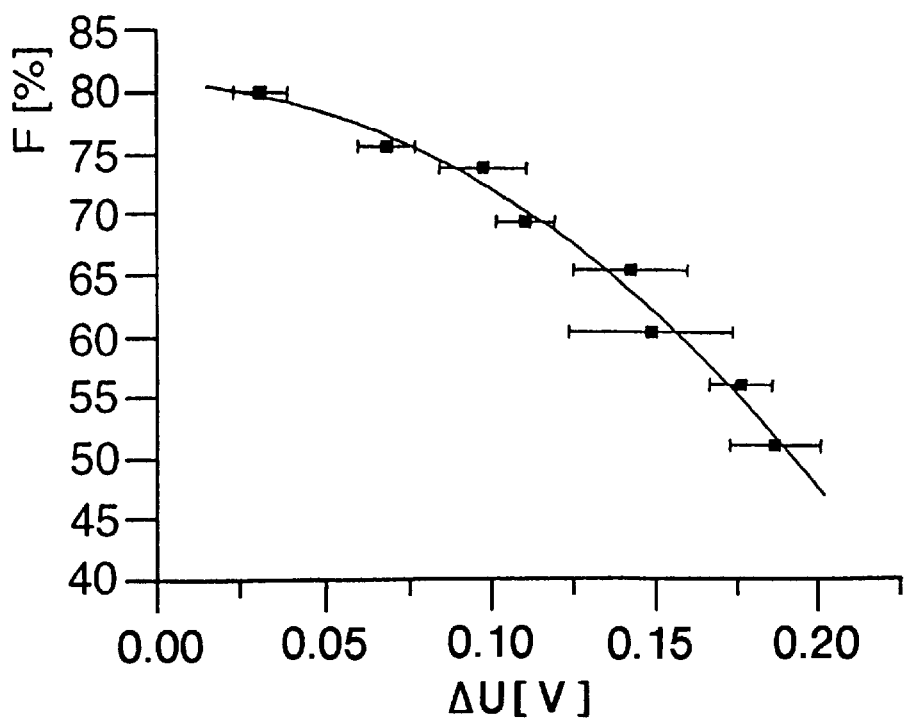
Figure 5:
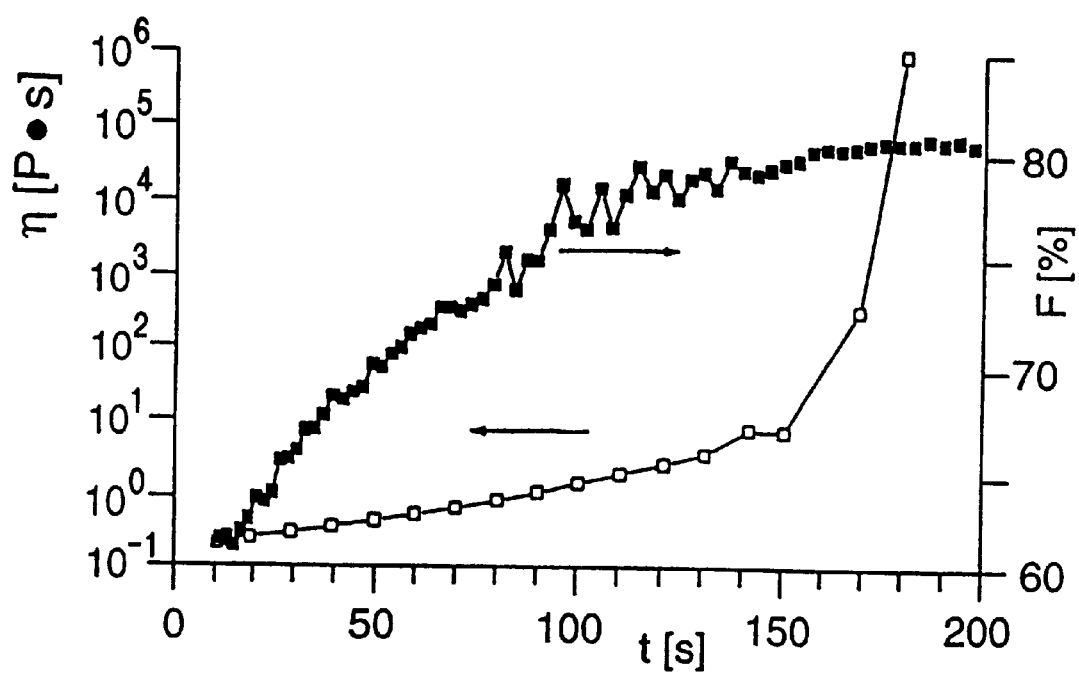

FIG. 1 shows a schematic diagram of a commercial rotational rheometer modified for the immobilization measurements, FIG. 2 shows a schematic diagram of a rotational rheometer according to FIG. 1 with additional integrated NIR probe for determining the water content, as a side view (FIG. 2a) and plan view (FIG. 2b), FIG. 3 shows the results of the measurement of the apparent viscosity as a function of the dewatering time for various thickener concentrations, FIG. 4 shows the calibration curve of the output signal of the NIR detector for coating slip B and FIG. 5 shows the results of the measurement of the simultaneous determination of apparent viscosity and solids content as a function of the dewatering time for coating slip B.

EXAMPLES

Example 1

A commercial rotational rheometer controlled as a function of shear stress, for example Bohlin$^R$ CS having a sample-receiving or measuring gap with plate-plate geometry is modified as follows (FIG. 1): A cylindrical, metallic hollow body 2 whose top surface consists of a perforated metal plate 3 is mounted on the stationary rheometer base plate 1. A connecting piece 4 which serves for connecting a vacuum pump is let into the lateral surface of said hollow body. The porous substrate 5, for example base paper, is fastened to the perforated metal plate 3 with the aid of a suitable clamping ring 6. This porous substrate 5 then serves as a lower bounding surface of the measuring gap. The opposite bounding surface is a metal plate 8 connected to the drive and detection system 7 of the rheometer. The gap in between is filled with the colloidal coating dispersion 9 to be investigated, for example with a paper coating slip.

By means of this arrangement, viscosity measurements can be carried out similarly to the procedure in the case of a measuring gap with a conventional base plate. The gap height may be varied from 20 $\mu$m to 2 mm, preferably from 50 to 500 $\mu$m.

The water in the coating slip 9 is absorbed by the base paper 5, preferably by applying a suitable reduced pressure, in particular from 200 to 500 mbar. Consequently, the coating slip 9 is concentrated similarly to the coating process during paper conversion. The viscosity increase associated with this process is measured with specification of a constant shear stress, preferably from 0.1 to 1000 Pa, particularly preferably from 10 to 100 Pa.

The curve of this viscosity change as a function of time characterizes the immobilization kinetics, which are dependent on the water retentivity of the respective paper coating slip and hence on its formulation and on the structure formation during the coating and dewatering process.

By varying the predetermined shear stress and, if required, the reduced pressure, different coating conditions can be simulated.

To avoid breaking the contact between coating slip 9 and metal plate 8 owing to the water loss during the measurement, the gap is overfilled (cf. FIG. 1) so that slip can subsequently flow into the gap from the outside. The outer region of the measuring gap is therefore always more moist than its interior, ie. the sample is inhomogeneous and the measured viscosities must be regarded as apparent or relative values. The salient point in the semilogarithmic plot of the viscosity as a function of time (FIG. 3) is defined as the immobilization point and the corresponding time as the immobilization time $t_{imm}$. Typically, a solid-like filter cake having a residual water content of 15–20% is present in the inner region of the sample gap after the immobilization.

The measuring method described above is not restricted to the characterization of the immobilization of a paper coating slip by penetration of water into the base paper to be coated. It is also possible to investigate other (including nonaqueous) coating dispersions (eg. adhesives, mortar) in a similar manner. Instead of the base paper, the respective substrate (eg. clay plate, glass frit) can be used as the rheometer base plate.

Example 2

The apparatus according to Example 1 is improved by integrating a fiber optic scattered light measuring system according to EP-B1-0 472 899 into the perforated metal plate 3 of the modified rheometer (FIG. 2). This makes it possible to measure the variation of the water content with time, simultaneously with the viscosity determination.

The light passed from a broadband light source 10, preferably a halogen light source, into a low-OH quartz fiber, preferably a fiber bundle composed of 200 $\mu$m fibers, to the measuring site is scattered by the product, scattered back into the parallel receiving fibers and passed to the detector 11. The sensor tip 13 of the fiber optic scattered light measuring system projects through the perforated metal plate 3 and the porous substrate 5 into the colloidal coating dispersion 9.

For the concentrations investigated, the arrangement of the reflection at a defined angle between transmitter/receiver and the plane of the measurement of preferably 11° permits low-reflection measurement of diffuse back-scattering by the product at a depth of penetration of a few $\mu$m.

The absorption of the NIR radiation by the water is due to the excitation of the second harmonic of the OH vibration. The light is absorbed in a broad band at 1470±20 nm to achieve the required signal amplitude. For the calibration of the product scattering without water absorption, a measurement is simultaneously carried out in a spectral wavelength range lying close to the absorption band but exhibiting no absorption, preferably at 1300 nm or 1700 nm. To be able to carry out measurements simultaneously at a plurality of wavelengths, the light is selected not on the transmission side but on the detection side.

In addition, the intensity of the light source at the selected wavelengths (in this case 1470 nm and 1700 nm) is determined. This makes it possible to eliminate signal fluctuations due to drifting of the light source. The stability of the other components is guaranteed by the user.

By means of suitable holes around the measuring surface which, with a diameter of 4 mm, is kept very small, the dewatering is hindered only to a small extent directly at the measuring site. Owing to pronounced shearing, the product is moved past the sensor tip 13 located close to the wall in the plane of the porous substrate 5, averaging over the total product present on the corresponding ring being achieved. Suitable perforation of the paper is necessary at the measuring site in order to be able to introduce the light directly into the coating dispersion 9.

The measuring system is modular. This makes it possible rapidly to adapt spectral range, fiber material, evaluation algorithm and installation environment in a wide range to the requirements of new tasks.

Measurements are made at a rate required for the investigation, ie. up to 30 measurements/second.

Owing to the small area of the sensor tip 13, it is also possible to integrate a plurality of such sensors into the rheometer base plate in a preferred procedure. As a result, the dewatering kinetics can also be determined as a function of location.

Immobilization measurement

The effect of the thickener Sterocoll$^R$ FD on the immobilization behavior of a paper coating slip with CaCO$_3$ as pigment (coating slip formulation A) was determined using the apparatus described below and under the stated conditions, by means of the method according to the invention.

Formulation for coating slip A:

70 parts by weight of Hydrocarb$^R$ 60 (CaCO$_3$ pigment)

30 parts by weight of Hydrocarb$^R$ 90 (CaCO$_3$ pigment)

10 parts by weight of Styronal$^R$ LD 615 (styrene/butadiene/acrylonitrile copolymer dispersion)

x parts by weight of thickener Sterocoll$^R$ FD (acrylate/acrylic acid copolymer)

Solids content: 62%, pH: 8.5–9.

Measuring instrument: Rotational rheometer controlled as a function of shear stress BOHLIN$^R$ CS Measurement geometry: Plate-plate Upper plate: Stainless steel, diameter 35 mm Base plate: Nitrocellulose filter from Schleicher & Schüll, pore size 5 μm, total diameter 50 mm, usable diameter 42 mm Holder: Perforated brass plate Gap height: 200 μm Shear stress: 100 Pa Pressure: 250 mbar (under the filter paper), 950 mbar (above paper coating slip)

Temperature of measurement: 25° C.

The development of the apparent viscosity as a function of time after the beginning of the dewatering process is shown in FIG. 3 for the thickener concentrations stated in Table 1. t=0 designates the beginning of the dewatering as a result of switching on the reduced pressure.

The viscosity curves show a characteristic salient point. A characteristic immobilization time $t_{imm}$ can be determined from the point of intersection of the tangents to the front and rear branches of the respective curves (see FIG. 3).

In the present example, the time $t_{imm}$ increases dramatically with increasing thickener concentration (Table 1).

Table 1: Dependence of the immobilization time $t_{imm}$ on the thickener concentration

| x (thickener concentration in %) | $t_{imm}[s]$ |
|---|---|
| 0.4 | 220 |
| 0.6 | 420 |
| 0.8 | 635 |

It is therefore evident that the water retentivity of these coating slip formulations increases substantially with increasing thickener concentration, in agreement with the real behavior in the coating process.

Determination of water content by fiber optic NIR spectroscopy

The light intensity registered in the detector 11 is output in the form of a voltage signal. The water content of the sample is linked to the voltage difference ΔU which is obtained from the different intensities of the light reflected at 1470 nm and 1700 nm.

Calibration of the voltage signal:

Samples of the same formulation with different solids contents are required for preparing the calibration curve. For the coating slip B mentioned here as an example, these calibration samples were prepared by suitable dilution of a starting sample having a solids content of 80.5%.

Formulation for coating slip B:

100 parts by weight of Hydrocarb$^R$ OG (CaCO$_3$ pigment)

0.4 part by weight of Polysalz$^R$ SR (Polyacrylic acid salt)

0.1 part by weight of NaOH 10 parts by weight of Styronal$^R$ LD 615 (styrene/butadiene/acrylonitrile copolymer dispersion)

0.5 part by weight of Sterocoll$^R$ FD (acrylate/acrylic acid copolymer)

The solids content F of the individual samples was plotted as a function of the voltage difference ΔU measured in each case (FIG. 4). By fitting a 2nd degree polynomial to the pairs of values thus determined, a calibration function (valid for coating slip B) was determined. The voltage differences ΔU measured during the dewatering process can be converted into solids contents using this function.

The calibration function depends to a great extent on the apparatus specifications and must be redetermined with every modification of the measuring set-up (aging/replacement of the halogen lamp, change/drift of the test amplifier, etc.).

The result of the simultaneous determination of the solids content F ■ and of the apparent viscosity η □ as a function of the dewatering time for coating slip B is shown in FIG. 5, t=0 denoting the beginning of dewatering as a result of switching on the reduced pressure.

We claim:

1. A method for determining the immobilization of a colloidal coating dispersion comprising:

applying the colloidal coating dispersion (9) to a porous substrate (5) thereby forming a bounding surface of the measuring gap of a rheometer, and measuring the change in the viscosity of the colloidal coating dispersion as a function of time.

2. A method as claimed in claim 1, wherein the change in the viscosity as a function of time is measured with specification of a constant shear stress or shear rate.

3. A method as claimed in claim 1, wherein the height of the measuring gap is set at from 20 μm to 2 mm.

4. A method as claimed in claim 1, wherein reduced pressure is applied to that surface of the porous substrate (5) which is opposite the surface carrying the colloidal coating dispersion (9).

5. A method as claimed in claim 1, wherein the loss of liquid phase in the colloidal coating dispersion (9) as a function of time is measured by a sensor which projects into the colloidal coating dispersion (9).

6. A method as claimed in claim 5, wherein the sensor is part of a fiber optic scattered light measuring system.

7. A method as claimed in claim 5, wherein the fiber optic scattered light measuring system operates in the NIR radiation range.

8. The method of claim 5, wherein the colloidal coating dispersion is a paper coating slip and the porous substrate is base paper.

9. A method as claimed in claim 1 wherein the colloidal coating dispersion is a paper coating slip and the porous substrate is a base paper.

10. A method as claimed in claim 1, wherein the height of the measuring gap is set at from 50 μm to 500 μm.

11. Apparatus for determining the immobilization of a colloidal coating dispersion on application to a porous substrate, wherein the porous substrate (5) which causes the immobilization by absorbing a part of the liquid phase of the coating dispersion (9) forms a bounding surface of a rheometer gap.

12. Apparatus as claimed in claim 11, wherein a sensor projects into the colloidal coating dispersion (9) and is used for measuring the loss of liquid phase as a function of time in the colloidal coating dispersion (9).

* * * * *